(12) United States Patent
Al-Abed

(10) Patent No.: US 9,567,306 B2
(45) Date of Patent: Feb. 14, 2017

(54) INHIBITION OF MACROPHAGE MIGRATION INHIBITORY FACTOR IN MELANOMA AND COLON CANCER

(71) Applicant: THE FEINSTEIN INSTITUTE FOR MEDICAL RESEARCH, Manhasset, NY (US)

(72) Inventor: Yousef Al-Abed, Dix Hills, NY (US)

(73) Assignee: The Feinstein Institute for Medical Research, Manhasset, NY (US)

(*) Notice: Subject to any disclaimer, the term of this patent is extended or adjusted under 35 U.S.C. 154(b) by 48 days.

(21) Appl. No.: 14/740,695

(22) Filed: Jun. 16, 2015

(65) Prior Publication Data

US 2015/0361058 A1    Dec. 17, 2015

Related U.S. Application Data

(60) Provisional application No. 62/013,143, filed on Jun. 17, 2014.

(51) Int. Cl.
| | | |
|---|---|---|
| *C07D 261/08* | (2006.01) | |
| *C07D 261/04* | (2006.01) | |
| *C07C 249/12* | (2006.01) | |
| *A61K 45/06* | (2006.01) | |
| *A61K 31/42* | (2006.01) | |

(52) U.S. Cl.
CPC ............. *C07D 261/08* (2013.01); *A61K 31/42* (2013.01); *A61K 45/06* (2013.01); *C07C 249/12* (2013.01); *C07D 261/04* (2013.01)

(58) Field of Classification Search
CPC .......................... C07D 261/08; C07D 261/04
See application file for complete search history.

(56) References Cited

U.S. PATENT DOCUMENTS

| | | | |
|---|---|---|---|
| 7,491,740 B2 * | 2/2009 | Al-Abed | ............. A61K 31/421 514/378 |
| 8,193,247 B2 | 6/2012 | Al-Abed | |
| 8,362,053 B2 | 1/2013 | Al-Abed | |
| 8,618,147 B2 | 12/2013 | Al-Abed | |
| 8,742,173 B2 | 6/2014 | Al-Abed | |
| 2003/0008908 A1 * | 1/2003 | Al-Abed | ............. A61K 31/421 514/378 |
| 2008/0305118 A1 | 12/2008 | Al-Abed | |
| 2009/0318509 A1 | 12/2009 | Al-Abed | |
| 2014/0242091 A1 | 8/2014 | Miller et al. | |

FOREIGN PATENT DOCUMENTS

WO    WO 2011066482 A2 *    6/2011    ........... C07D 261/04

* cited by examiner

*Primary Examiner* — Nyeemah A Grazier
(74) *Attorney, Agent, or Firm* — Amster, Rothstein & Ebenstein LLP

(57) ABSTRACT

Compounds and compositions are provided which inhibit MIF. Methods of treatment of melanoma and colon cancers are also provided.

20 Claims, 10 Drawing Sheets

INHIBITION OF MACROPHAGE MIGRATION INHIBITORY FACTOR IN MELANOMA AND COLON CANCER

CROSS-REFERENCE TO RELATED APPLICATIONS

This application claims benefit of U.S. Provisional Application No. 62/013,143, filed Jun. 17, 2014, the contents of which are hereby incorporated by reference.

BACKGROUND OF THE INVENTION

Throughout this application various patents and other publications are referred to in parenthesis. Full citations for the references may be found at the end of the specification. The disclosures of these patents and all patents, patent application publications and books referred to herein are hereby incorporated by reference in their entirety into the subject application to more fully describe the art to which the subject invention pertains.

Macrophage migration inhibitory factor (MIF), a cytokine first identified in 1966, is expressed fairly ubiquitously and has both extracellular and intracellular roles (reviewed in (1)). MIF has been implicated in autoimmune and infectious disease, and cancer (reviewed in (1)). The causative role of MIF in cancer progression was initially linked to its increased expression by a variety of cancer cells, including prostate, colon, hepatocellular, lung, ovarian, in addition to melanoma, glioblastoma and neuroblastoma (2). In these cancers, MIF overexpression has been associated with a concomitant increase in: (a) tumor invasion/migration, (b) metastasis and (c) angiogenesis. More recent data have additionally identified the role of the host MIF in regulating tumor growth. In support of the latter, the role of MIF in regulating tumor angiogenesis in the B16-F10 melanoma model has recently been investigated (3). A combination either of B16-F10 or of shRNA targeting of MIF in the same melanoma cells with a MIF knockout (−/−) genetic background, resulted in significant reduction of tumor growth (by 47%), when compared to wild-type mice. Furthermore, reduced growth of CT26 colon tumors (by 75%) in MIF−/− mice was reported (4). Finally, host macrophage-produced MIF was shown to polarize tumor-associated macrophages (TAMs) towards an immunosuppressive M2 phenotype, whereas MIF inhibition or gene loss (MIF−/−) reversed TAM functionalities to M1-type (5). These studies, in conjunction with the previous reports, establish MIF as a promising anticancer drug-target.

An increase of MIF levels positively correlates with a poor prognosis in cancer (6-8). Anti-MIF neutralizing antibodies (Abs), MIF-directed siRNA/shRNA or anti-sense oligonucleotides and compounds hindering MIF secretion have been tested in vitro and in preclinical models with notable results (9,10). A more attractive approach to decrease MIF upregulation is the utilization of small molecule MIF inhibitors, which advantageously block the activity of both cancer cell- and host cell-secreted MIF. ISO-1, the "gold standard" inhibitor of MIF, was designed to selectively ligate the tautomerase catalytic site of MIF which is known to neutralize its pro-inflammatory activity (1,11, 12). In vitro MIF reduction by ISO-1, has been reported to effectively reduce cancer cell proliferation, migration, and invasion of the human lung adenocarcinoma A549 (10,13) decrease the proliferation and invasiveness of prostate cancer DU-145 cells (9), restore contact inhibition of proliferation of LN229 and LN-18 glioblastoma cells (14), reduce cell migration and invasion of HS683 glioma cells (15), and suppress the proliferation of the murine colorectal cancer cells CT-26 (16). Previous studies have also addressed the role of ISO-1 in prostate and colorectal cancer in vivo (9,16). In both mouse models, ISO-1 treatment resulted in significant reduction of the tumor volume or weight, despite the lack of an optimal dosing regimen.

The present invention address the need for improved MIF inhibitors and improved cancer treatments employing MIF inhibitors.

SUMMARY OF THE INVENTION

A compound is provided having the following structure:

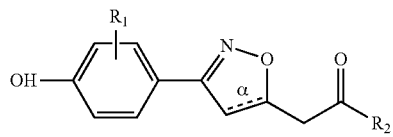

wherein bond α is either present or absent, and when bond α is absent $R_1$ is a monohalo substitution or a dihalo substitution, and when bond α is present $R_1$ is H, a monohalo or a dihalo,
wherein $R_2$ is a C1-C10 alkyl, a C2-C10 alkenyl, a C2-C10 alkynyl, an aryl, a heterocyclic, or —C(O)(OH),
or a stereoisomer thereof or a pharmaceutically acceptable salt thereof.

Also provided is a process for making a compound of the invention as described herein comprising:
a) contacting 3-fluoro-4-hydroxybenzaldoxime with a chlorinating agent so as to produce a chloro oxime thereof; and
b) contacting the chloro oxime with 4-penten-2-one followed by addition of suitable base thereto, so as to produce the compound.

Also provided is a method of treating a tumor in a subject comprising administering to the subject the compound or stereoisomer or pharmaceutically acceptable salt or composition as described herein, in an amount effective to treat a tumor in a subject.

Also provided is a method of inhibiting progression of a tumor in a subject comprising administering to the subject the compound or stereoisomer or pharmaceutically acceptable salt or composition as described herein, in an amount effective to inhibit progression of a tumor in a subject.

Also provided is a method of stimulating expansion of an anti-tumor reactive effector cell in a subject comprising administering to the subject the compound or stereoisomer or pharmaceutically acceptable salt or composition as described herein, in an amount effective to stimulate expansion of an anti-tumor reactive effector cell.

Also provided is a method of reducing an inflammation in a subject comprising administering to the subject the compound or stereoisomer or pharmaceutically acceptable salt as described herein, or one of the compositions as described herein, in an amount effective to reduce inflammation in a subject.

Also provided is a method of manufacturing a medicament comprising admixing the compound or stereoisomer or pharmaceutically acceptable salt as described herein, and a pharmaceutically acceptable carrier.

Also provided is a pharmaceutical composition comprising the compound or stereoisomer or pharmaceutically acceptable salt as described herein, and a pharmaceutically acceptable carrier.

Also provided is a method of treating a tumor in a subject comprising administering to the subject the compound or stereoisomer or pharmaceutically acceptable salt as described herein, or one of the compositions as described herein, and an anti-tumor agent, in an amount effective to treat a tumor in a subject.

Also provided is a method of treating an autoimmune disease in a subject comprising administering to the subject the compound or stereoisomer or pharmaceutically acceptable salt as described herein, or one of the compositions as described herein, and an anti-autoimmune agent, in an amount effective to treat an autoimmune disease in a subject.

Additional objects of the invention will be apparent from the description which follows.

DETAILED DESCRIPTION OF THE INVENTION

Figure 1:
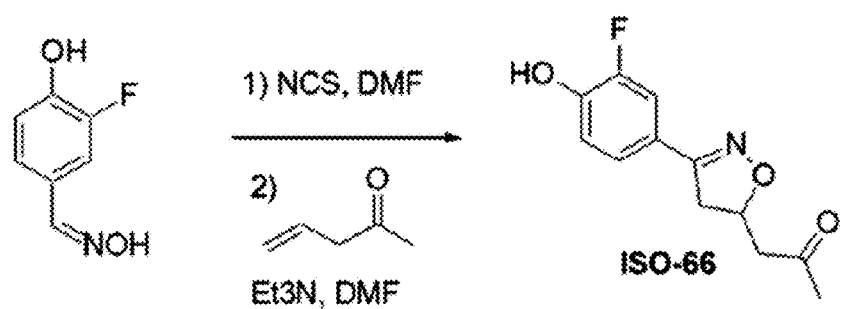
FIG. 1. Synthesis of ISO-66 and $IC_{50}$ in MIF tautomerase assay of ISO-1, ISO-66 and the prodrug of ISO-66 (ISO-1: 18.2+2.8 μM; ISO-66: 1.5+0.4 μM; prodrug of ISO-66: 1.8+0.1 μM).
Figure 1:
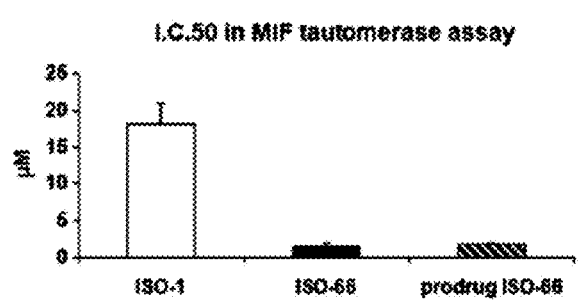
Figure 1:
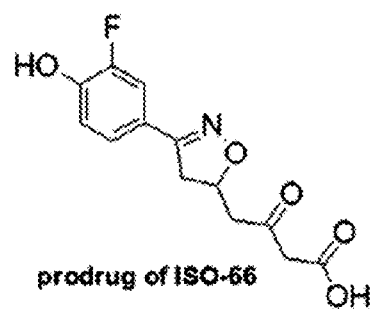

A compound is provided having the following structure:

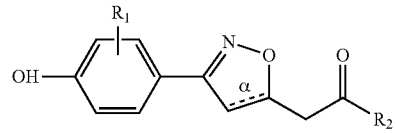

wherein bond α is either present or absent, and when bond α is absent $R_1$ is a monohalo substitution or a dihalo substitution, and when bond α is present $R_1$ is H, a monohalo or a dihalo, wherein $R_2$ is a C1-C10 alkyl, a C2-C10 alkenyl, a C2-C10 alkynyl, an aryl, a heterocyclic, or —C(O)(OH), or a stereoisomer thereof or a pharmaceutically acceptable salt thereof.

In an embodiment, $R_1$ is H. In an embodiment, $R_1$ is a monohalo substitution. In an embodiment, $R_1$ is a dihalo substitution. A monohalo substitution is one halogen attached to the ring. A dihalo substitution is two separate halogens attached to the ring. In an embodiment, the halogens of the dihalo substitution are both of the same type. In an embodiment, the halogens of the dihalo substitution are of differing types. The halogen of the monohalo or dihalo can be F, Br, Cl or I. In an embodiment, the halogen is F.

In an embodiment, $R_2$ is a C1-C10 alkyl. In a preferred embodiment, $R_2$ is a C1 alkyl. In an embodiment, $R_2$ is a C2-C10 alkenyl. In an embodiment, $R_2$ is a C2-C10 alkynyl. In an embodiment, the alkyl, alkenyl or alkynyl are unsubstituted. In an embodiment, $R_2$ is aryl. In an embodiment, $R_2$ is a heterocyclic. In an embodiment, the aryl is unsubstituted. In an embodiment, the heterocycle are unsubstituted. In an embodiment, $R_2$ is —C(O)(OH).

In embodiments of the invention, the compound has the following structure:

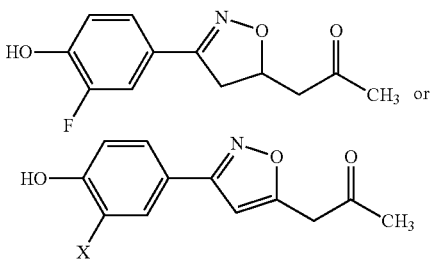

where X=H or F,
or is a stereoisomer or pharmaceutically acceptable salt of one thereof.

A preferred compound has the structure:

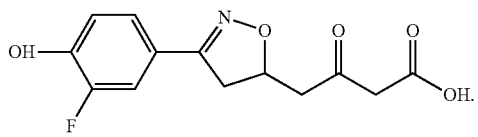 [SMILES: O=C(O)CC(=O)CC1CC(c2ccc(O)c(F)c2)=NO1]

A stereoisomer or pharmaceutically acceptable salt of such structure are embodiments of the invention.

A composition is provided comprising a compound, stereoisomer thereof or pharmaceutically acceptable salt thereof, as disclosed herein, and a pharmaceutically acceptable carrier. Preferably, the composition is a pharmaceutical composition.

The compounds of the present invention include all hydrates, solvates, and complexes of the compounds used by this invention.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include carbon-13 and carbon-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein. In an embodiment, the carbon in the structures shown herein is $^{12}C$.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein. In an embodiment, the hydrogen in the structures shown herein is $^1H$.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The term "heterocyclic" as used herein refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The compounds of the instant invention may be in a salt form. As used herein, a "salt" is salt of the instant compounds which has been modified by making acid or base, salts of the compounds. In the case of compounds used for treatment of cancer, tumor, melanoma or autoimmune disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

A process for making a compound of the invention as described herein is provided comprising:
a) contacting 3-fluoro-4-hydroxybenzaldoxime
with a chlorinating agent so as to produce a chloro oxime thereof; and
b) contacting the chloro oxime with 4-penten-2-one followed by addition of suitable base thereto,
so as to produce the compound.

In an embodiment of the process, the suitable base in step b) is triethylamine. In an embodiment of the process, the suitable base is in a suitable solvent. In an embodiment, the suitable solvent is dimethylformamide (DMF). In an embodiment of the process, the 3-fluoro-4-hydroxybenzaldoxime is in an anhydrous solvent. In an embodiment of the process, the anhydrous solvent is anhydrous dimethylformamide. In an embodiment of the process, the chlorinating agent is N-chlorosuccinimide. In an embodiment of the process, the 4-penten-2-one is made by a process comprising oxidizing 4-penten-2-ol with pyridinium chlorochromate (PCC) in a suitable solvent. In an embodiment, the suitable solvent is dichloromethane (DCM).

In an embodiment of the process, in step b), reactants are stirred under $N_2$ at a suitable temperature. The temperature can be room temperature.

A process is provided as described and further comprising purifying the compound by FCC.

In an embodiment, the solvent is removed in vacuo and the residue is taken up in EtOAc. In an embodiment, the EtOAc solution is washed with 0.5 N HCl, water, brine, and dried with anhydrous MgSO$_4$. In an embodiment, the filtrate is evaporated to dryness and the residue purified by FCC (hexane:EtOAc 4:3).

Also provided is a method of manufacturing a medicament comprising admixing the compound or stereoisomer or pharmaceutically acceptable salt as described herein, and a pharmaceutically acceptable carrier.

Also provided is a pharmaceutical composition comprising the compound or stereoisomer or pharmaceutically acceptable salt as described herein, and a pharmaceutically acceptable carrier.

Also provided is a method of treating a tumor in a subject comprising administering to the subject the compound or stereoisomer or pharmaceutically acceptable salt or composition as described herein, in an amount effective to treat a tumor in a subject.

In a preferred embodiment, the tumor can comprise a melanoma. In a preferred embodiment, the tumor can comprise a colon cancer.

Also provided is a method of inhibiting progression of a tumor in a subject comprising administering to the subject the compound or stereoisomer or pharmaceutically acceptable salt or composition as described herein, in an amount effective to inhibit progression of a tumor in a subject. In an embodiment, the subject has a melanoma. In an embodiment, the subject has a colon cancer.

In an embodiment of the methods herein, the melanoma is a stage 0 melanoma. In an embodiment, the melanoma is a stage I melanoma. In an embodiment, the melanoma is a stage II melanoma. In an embodiment, the melanoma is a stage III melanoma. In an embodiment, the melanoma is a stage IV melanoma.

In an embodiment of the methods herein, the colon cancer is a stage I colon cancer. In an embodiment, the colon cancer is a stage IIa colon cancer. In an embodiment, the colon cancer is a stage IIb colon cancer. In an embodiment, the colon cancer is a stage IIIa colon cancer. In an embodiment, the colon cancer is a stage IIIb colon cancer. In an embodiment, the colon cancer is a stage IIIc colon cancer. In an embodiment, the colon cancer is a stage IV colon cancer.

Also provided is a method of stimulating expansion of an anti-tumor reactive effector cell in a subject comprising administering to the subject the compound or stereoisomer or pharmaceutically acceptable salt or composition as described herein, in an amount effective to stimulate expansion of an anti-tumor reactive effector cell.

Also provided is a method of reducing an inflammation in a subject comprising administering to the subject the compound or stereoisomer or pharmaceutically acceptable salt as described herein, or one of the compositions as described herein, in an amount effective to reduce inflammation in a subject.

Also provided is a method of treating a tumor in a subject comprising administering to the subject the compound or stereoisomer or pharmaceutically acceptable salt as described herein, or one of the compositions as described herein, and an anti-tumor agent, in an amount effective to treat a tumor in a subject. In an embodiment, the tumor is a colon cancer. In an embodiment, the tumor is a melanoma.

Also provided is a method of treating an autoimmune disease in a subject comprising administering to the subject the compound or stereoisomer or pharmaceutically acceptable salt as described herein, or one of the compositions as described herein, and an anti-autoimmune agent, in an amount effective to treat an autoimmune disease in a subject. There are many MIF inhibitors in the art that have been shown to be effective in the tautomerase assay herein and subsequently useful in treating autoimmune diseases. Similarly, the proven effectiveness of the present compounds in the tautomerase assay indicates their suitability for treating autoimmune diseases, including inflammatory autoimmune diseases. Autoimmune diseases treatable with the compounds and compositions of the invention include acute disseminated encephalomyelitis (ADEM), alopecia areata, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Behçet's disease, celiac disease, Chagas disease, cold agglutinin disease, Crohn's disease, dermatomyositis, diabetes mellitus type 1, eosinophilic fasciitis, gastrointestinal pemphigoid, Goodpasture's syndrome, Grave's syndrome, Guillain-Barré syndrome, Hashimoto's encephalopathy, Hashimoto's thyroiditis, lupus erythematosus, Miller-Fisher syndrome, mixed connective tissue disease, myasthenia gravis, *pemphigus vulgaris*, pernicious anaemia, polymyositis, psoriasis, psoriatic arthritis, relapsing polychondritis, rheumatoid arthritis, rheumatic fever, Sjögren's syndrome, temporal arteritis, transverse myelitis, ulcerative colitis, undifferentiated connective tissue disease, vasculitis, or Wegener's granulomatosis.

In a preferred embodiment of the methods, the administered compound has the structure:

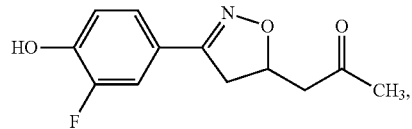 [SMILES: CC(=O)CC1CC(c2ccc(O)c(F)c2)=NO1]

or the stereoisomer or pharmaceutically acceptable salt thereof or composition comprising such is administered.

The compound or stereoisomer or pharmaceutically acceptable salt or composition can be administered as required. In an embodiment, the compound or stereoisomer or pharmaceutically acceptable salt or composition is administered daily for a predetermined amount of time. In an embodiment, the compound or stereoisomer or pharmaceutically acceptable salt or composition is administered twice daily for a predetermined amount of time. In an embodiment, the compound or stereoisomer or pharmaceutically acceptable salt or composition is administered continuously for a predetermined amount of time. In an embodiment, the predetermined amount of time is at least one day. In an embodiment, the predetermined amount of time is at least one week. In an embodiment, the predetermined amount of time is at least two weeks. In an embodiment, the predetermined amount of time is at least one month.

In an embodiment, the compounds of the invention are also provided as a pharmaceutically acceptable ester. The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates. In some embodiments, the esters are cleaved by enzymes such as esterases.

In an embodiment, for example wherein the compound, stereoisomer, salt or ester thereof is being used for treating a melanoma, the composition in which the active ingredient is administered may include a penetration enhancer. The term "penetration enhancer" as used herein is a non-toxic agent that improves bioavailability of a topical composition. In some embodiments, a penetration enhancer is known to accelerate the delivery of a substance through the skin (e.g., disrupting the barrier function of the skin without compromising its barrier effects on microorganisms and toxins). Typically, a penetration enhancer is selected to be non-toxic to skin of the intended recipient (e.g., human). A penetration enhancer is also desirably compatible with any pharmaceutically active agent with which it is administered. Representative penetration enhancers include, for example, and without limitation, such agents as 1-substituted azacycloheptane-2-ones (e.g., 1-n-dodecylcyclazacycloheptan-2-one, available under the trademark Azone™ from Whitby Research Incorporated, Richmond, Va.), dipolar-aprotic solvents (e.g., N,N-dimethylacetamide ("DMA"), decylmethylsulfoxide ("$C_{10}$ MSO"), dimethyl formamide ("DMF"), dimethylsulfoxide ("DMSO") and N-methyl-2-pyrrolidone ("NMP")), phospholipids (e.g., allantoin, fatty acid alcohols, lecithin, alcohols including glycerols such as polyethylene glycol monolaurate ("PGML"), glycerol monolaurate ("GML"), urazole, and the like). Penetration enhancer also can be a vegetable oil, such as, but not limited to, corn oil, cottonseed oil, safflower oil, and olive oil. Additional penetration enhancers generally can be found in Remington: The Science and Practice of Pharmacy, 20.sup.th ed. (Gennaro, A. R., et al., eds.) Lippincott Williams & Wilkins: Philadelphia (2000), which is incorporated herein by reference.

In general, the "effective amount" of an active agent (e.g., a therapeutic agent, composition, and/or formulation) are an amount effective to achieve a stated effect refers to an amount sufficient to elicit the desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of one or more symptoms of the disease, disorder, and/or condition. As will be appreciated by those of ordinary skill in this art, and effective amount of a substance may vary depending on such factors as the desired biological endpoint, the substance to be delivered, the pharmacokinetics of the compound, the target cell or tissue, the disease being treated, the mode of administration, and the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, a therapeutically effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect.

Routes of administration encompassed by the methods of the invention include the following individual routes, and any subset thereof, auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, urethral, and vaginal administration. For autoimmune diseases, one embodiment includes administration into the organ or organs or tissue or tissues affected by the autoimmune diseases. For melanoma, one embodiment includes administration into the melanoma directly, e.g. by topical administration. For colon cancer, one embodiment includes administration into the colon or directly into the colon cancer tumor.

In an embodiment of the methods, the subject is human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL RESULTS

Introduction

Macrophage migration inhibitory factor (MIF) is a pleiotropic pro-inflammatory cytokine, which possesses a contributing role in cancer progression and metastasis and thus, is now considered a promising anticancer drug-target. Many MIF-inactivating strategies have proven successful in delaying cancer growth. Here, synthesis of a novel, highly stable, small-molecule MIF-inhibitor is disclosed, namely, ISO-66, which shows improved characteristics over ISO-1. The MIF:ISO-66 co-crystal structure demonstrated that ISO-66 ligates the tautomerase active site of MIF, which has previously been shown to play an important role in its biological functions. In vitro, ISO-66 enhanced specific and non-specific anti-cancer immune responses, whereas prolonged administration of ISO-66 in mice with established syngeneic melanoma or colon cancer was non-toxic and resulted in a significant decrease in tumor burden. Subsequent ex-vivo analysis of mouse splenocytes revealed that the observed decrease in tumor growth rates was likely mediated by the selective in vivo expansion of anti-tumor-reactive effector cells induced by ISO-66. Compared to other MIF-inactivating strategies employed in vivo, the anticancer activity of ISO-66 is demonstrated to be of equal or better efficacy. Targeting MIF, via highly specific and stable compounds, such as ISO-66, can be effective for cancer treatment and stimulation of anticancer immune responses.

Materials and Methods

Preparation of ISO-66: All solvents were HPLC-grade from Fisher Scientific. Silica gel (Selecto Scientific, 32-63 μm average particle size) was used for flash column chromatography (FCC). Aluminum-backed Silica Gel 60 with a 254 nm fluorescent indicator TLC plates were used. Spots on TLC plates were visualized under a short wavelength UV lamp or stained with I2 vapor. NMR spectra were collected on a Jeol Eclipse 400 spectrometer at 400 MHz for 1H NMR spectra and 100 MHz for the 13C NMR spectra. Coupling constants are reported in Hertz (Hz), and chemical shifts are reported in parts per million (ppm) relative to deuterated solvent peak. The coupling constants (J) are measured in Hertz (Hz) and assigned as s (singlet), d (doublet), t (triplet), m (multiplet) and br (broad). High-resolution mass spectra were carried out at the Mass Spectrometry Facility at the Hunter College of the City University of New York.

To a solution of 3-fluoro-4-hydroxybenzaldoxime (1 g; 6.45 mmol) in anhydrous DMF (120 mL) was added NCS (1.03 g; 7.74 mmol). The reaction mixture was stirred for 5 h at room temperature affording the chloro oxime. To this solution, 4-penten-2-one (1.0 mL; 9.7 mmol) (oxidize 4-penten-2-ol with PCC in DCM) was added, followed by the dropwise addition of triethylamine (1.34 mL; 9.68 mmol) in DMF (12 mL). The reaction mixture was stirred under $N_2$ at room temperature for 48 h. The solvent was removed in vacuo and the residue was taken up in EtOAc. The EtOAc solution was washed with 0.5 N HCl, water, brine, and dried with anhydrous $MgSO_4$. The filtrate was evaporated to dryness and the residue was purified by FCC (hexane:EtOAc 4:3) to yield ISO-66 as a pale yellow solid (0.6 g; 39%). 1H NMR (500 MHz, Methanol-d4) δ 7.40 (d, 1H), 7.30 (d, 1H), 6.96 (m, 1H), 5.05 (m, 1H), 3.53 (m, 1H), 3.03 (m, 2H), 2.86 (m, 1H), 2.21 (s, 3H); 13C NMR (125 MHz, Methanol-d4) δ 31.43, 42.08, 79.24, 116.07, 116.23, 119.85, 123.54, 125.70, 149.46, 152.76, 154.68, 158.84, 209.48; HR-MS(ES) m/z (M+H) 238.0871 (found); 238.0873 (calculated). Compound KF III 53Y, the prodrug of ISO-66, was prepared from the ISO-acid chloride with bis-trimethylsilyl malonate via methods reported in the literature (17,18). KF III 53Y has better solubility than ISO-66, but undergoes fast decarboxlyation to form ISO-66 upon formulation in buffer.

MIF tautomerase inhibition assay: MIF tautomerase activity was measured using a UV-Visible spectrophotometer (SHIMADZU, UV1600U). A fresh stock solution of L-dopachrome methyl ester was prepared at 2.4 mM through oxidation of L-3,4-dihydroxyphenylalanine methyl ester with sodium periodate. 1 μL of MIF solution (800-900 μg/mL) and 1 μL of a dimethyl sulfoxide (DMSO) solution with various concentrations of the MIF inhibitor were added into a plastic cuvette (10 mm, 1.5 mL) containing 0.7 mL assay buffer (50 mM potassium phosphate, pH 7.2). Then, activated L-dopachrome methyl ester solution (0.3 mL) was added to the assay buffer mixture. Activity was determined at room temperature and spectrometric measurements were made every 5 sec at λ, =475 nm for total 20 sec, by monitoring the rate of decolorization of L-dopachrome in comparison to a standard solution.

Crystallization and X-ray Data Collection: Recombinant human MIF was expressed in *E. coli* and purified as described (19). Briefly, cells were lysed using a French Pressure Cell, the lysate was clarified by centrifugation, and the supernatant liquid was filtered with a 0.22 μm filter. The filtered supernatant was purified by ion-exchange in 20 mM Tris (pH 7.5), 20 mM NaCl using a DEAE and an SP column connected in series. MIF is found in the flow-through. Flow-through fractions were collected, and fractions containing pure MIF were pooled and concentrated.

A stock solution of 1.2 mM MIF in 20 mM Tris (pH 7.5), 20 mM NaCl, and a stock of 0.10 M KF III 53Y (the carboxylated derivative/prodrug, of ISO-66) in DMSO were used to prepare a solution of 1.1 mM MIF, 10 mM KF III 53Y, 18 mM Tris (pH 7.5), 18 mM NaCl, 10% DMSO. The KF III 53Y spontaneously decarboxylated non-enzymatically, forming ISO-66. Crystallization was performed using the hanging-drop vapor diffusion method. Two μL of MIF-ISO-66 complex were mixed with an equal volume of reservoir comprised of 2 M (NH4)2SO4, 0.1 M Tris (pH 7.5), 3% isopropanol. Crystals grew in three to five weeks. X-ray diffraction data were collected from a single crystal at station X29 of the National Synchrotron Light Source at Brookhaven National Laboratory. Crystal dimensions were approximately 0.40×0.25×0.23 mm. Immediately prior to mounting the crystal, it was soaked briefly in cryoprotective solution containing 2.25 M NaCl, 2 M (NH4)2SO4, 50 mM Tris (pH 7.5). An ω-sweep of 100° of data were collected with 1.0809 Å radiation. Data were processed using HKL2000. Data collection statistics are presented in Table 1.

TABLE 1

| Crystallographic data | |
|---|---|
| Integration and scaling | |
| Space group | P3$_1$21 |
| Unit cell | a = b = 95.46 Å, c = 104.55 Å, α = β = 90°, γ = 120° |
| Resolution, Å (highest shell) | 1.55 (1.61-155) |
| Unique reflections | 79,934 (7,885) |
| Completeness, % | 99.6 (99.2) |
| Redundancy | 5.8 (5.3) |
| Avg. I/Avg. σ | 33.2 (2.25) |
| R$_{merge}$ | 0.058 (0.534) |
| Refinement | |
| R (working) | 19.9% |
| R-free | 22.0% |
| RMS deviations from ideality[a] | |
| Bond lengths (Å) | 0.010 |
| Bond angles (°) | 1.273 |
| Average B-factors[b], Å$^2$ | |
| Overall | 25.577 |
| Protein (number of residues) | 24.061 (114 × 3 chains) |
| Water | 35.923 (281) |
| Chloride | 34.078 (6) |
| Sulfate | 28.648 (1) |
| Inhibitors | 39.299 (4) |

[a]Calculated by Refmac5, using reference values from Engh and Huber (43).
[b]Calculated using the Baverage program in the CCP4 suite (CCP41994).

Structure Determination: The program AMoRe was used for molecular replacement. Protein coordinates from the complex of MIF with OXIM-11 (20) was used as the search model. Refinement was performed primarily using the program CNS (21). Refmac5 was also used for refinement. Occupancy refinement was performed using CNS. Refined occupancies were normalized so that the sum of the occupancies of corresponding atoms was 1.0. A TLS model was employed in the Refmac5 refinement. The initial TLS model was found using the TLSMD web server. Manual manipulation of the model was performed using O and COOT. The structure was deposited into the RCSB Protein Data Bank. Crystallographic statistics are presented in Table 1.

Cell lines and culture conditions: The human FM3 (melanoma), HCT-116 (colorectal carcinoma), K562 (leukemia), Daudi (Burkitt's lymphoma), and the murine B16-F1 (melanoma), CT-26.WT (colorectal carcinoma), YAC-1 (lymphoma), WEHI 164 (fibrosarcoma) cell lines, peripheral blood mononuclear cells (PBMCs) and their subpopulations and mouse spleen cells were cultured in RPMI 1640, supplemented with 10% heat-inactivated fetal bovine serum (FBS), 2 mM L-glutamine, 10 mM Hepes, 50 μM β-mercaptoethanol, 5 μg/ml Gentamycin, 10 U/ml Penicillin and 10 U/ml Streptomycin (all from Lonza, Cologne, Germany) (thereafter referred to as complete medium), at 37° C., in a humidified 5% CO2 incubator. ISO-66 was dissolved in DMSO at 50 mM, aliquoted and stored at −20° C. Serial dilutions of stock solutions were freshly prepared prior to their use.

Cell isolation and separation: Buffy coats were collected from 7 healthy blood-donors. Prior to blood withdrawal, individuals gave their informed consent according to the regulations approved by the 2nd Peripheral Blood Transfusion Unit and Haemorophilic Centre, 'Laikon' General Hospital Institutional Review Board, Athens, Greece.

PBMCs were isolated by centrifugation over Ficoll-Histopaque (Lonza) density gradient, resuspended in complete medium or cryopreserved in FBS-10% DMSO for later use. Purified natural killer (NK; CD56+) cells were obtained using an immunomagnetic isolation procedure. Briefly, 5-10×106 PBMCs were incubated for 15 min at 4° C. with 20 μL of anti-CD56 monoclonal Ab conjugated to magnetic beads (Miltenyi Biotec, Auburn, Calif., USA). CD56+ cells were isolated by positive selection on an MS column (Miltenyi), according to the manufacturer's instructions. Purity of the isolated populations was tested by flow cytometry (FACSCalibur, Becton Dickinson, Mountain View, Calif., USA), using FITC- and PE-conjugated anti-CD3 and anti-CD56 monoclonal Abs (BD Pharmingen, San Diego, Calif., USA). In all cases, purity of the NK population was over 90%.

For lymphokine-activated killer (LAK) cell generation, PBMCs were seeded in 24-well plates (1×106 cells/mL; 2 mL/well) and cultured for 5 days in complete medium supplemented with 1000 IU/mL recombinant human interleukin (IL)-2 (Proleukin, Roche, Calif., USA). Culture medium containing IL-2 was renewed every other day. On day 5, LAK cells were harvested and tested as described.

Monocytes were isolated by seeding PBMCs in 6-well plates (5×106/mL; 3 mL/well) and let adhere for 2 h at 370 C. The non-adherent cell fraction (comprising >80% CD3+ cells as assessed by flow cytometry) was collected and cryopreserved for later use in T cell stimulation cultures.

Proliferation assay: FM3, HCT-116, B16-F1 and CT-26.WT cancer cells were seeded into 96-well U-bottom microplates (Costar, Cambridge, Mass., USA; 20-25×103 cells/mL; 200 μL/well) and pre-incubated for 24 h to adhere. ISO-66 was serially diluted at various concentrations (1 mM-0.04 μM), added to the wells and incubated for 72 h. All cultures were set in triplicates, whereas cultures set in complete medium or containing an equivalent amount of DMSO (2% v/v) or doxorubicin (0.5 μM; Sigma-Aldrich, Japan) were used as controls. For the last 18 h, 3[H]-thymidine (Amersham Pharmacia Biotech, Amersham, Bucks, UK) was added and inhibition of proliferation was determined as described (22).

Stimulation of PBMCs, NK, LAK and T cells with ISO-66: PBMCs were seeded in 48-well plates (1×10$^6$ cells/mL; 1 mL/well), ISO-66 was added at final concentrations of 1 mM-1 μM and cells were cultured for 3 days. PBMCs cultured in plain complete medium served as controls. NK cells were isolated by magnetic beads and used as effector cells (E) versus K562 (NK-sensitive) targets (T), in standard 51Cr release assays at an E:T ratio of 10:1. Similarly cultured LAK cells were also used as effectors versus K562 and Daudi (LAK-sensitive) targets at and E:T ratio of 50:1.

T cells were stimulated with a pool of tumor antigenic peptides, extracted from the cell surface of FM3 and HCT-116 (acid wash extract, AWE), as previously described (23). In brief, on day 0 monocytes were irradiated at 30 Gy, washed and co-incubated with autologous T cells, at a monocyte:lymphocyte ratio of 1:5. AWE extracted from 20×10$^6$ FM3 or HCT-116 cells and ISO-66 at a final concentration of 10 μM, was added to each well. Cultures set without ISO-66 served as controls. On day 5, lymphocytes were restimulated with autologous irradiated monocytes and FM3- or HCT-116-AWE. On days 2, 5, 7 and 9, IL-2 (40 IU/mL) and ISO-66 (10 μM) were added to the culture medium. T cells were harvested on day 11 and tested for their cytotoxic activity versus FM3, HCT-116 and Daudi targets, using standard $^{51}$Cr-release assays, at an E:T ratio of 50:1.

In vivo melanoma and colon cancer mouse models: Female mice, 6-8 weeks of age, 15-20 g of weight, of the strains C57BL/6 and Balb/C were purchased from Harlan Laboratories (Udine, Italy). All mice were maintained under conditions and protocols in accordance with Law 2015/27/ 2.1992, Presidential Decree 160/3.5.1991 and the Directive 86/609/EEC/24.11.1986 of the Council of Europe on Animal Welfare. The study was approved by the Ethics and Biosafety Committee, Subcommittee on Ethics, Department of Biology, University of Athens and all experiments were conducted following the guidelines of the aforementioned committee.

B16-F1 (syngeneic to C57BL/6 mice) and CT-26.WT (syngeneic to Balb/C mice) were expanded to sufficient numbers in complete medium. On day 0, C57BL/6 and Balb/C mice were subcutaneously (sc) inoculated with 1×10$^5$ B16-F1 or 1×10$^6$ CT-26.WT (in 250 μL PBS), respectively, and mice of each strain were randomly assigned to 5 groups (8 mice/group). On days 12-14, when tumors were palpable, and for 20 consecutive days, mice received intraperitoneally (ip) PBS or DMSO (control groups), or ISO-66 (all diluted in 300 μL PBS) once daily. ISO-66 was administered at 180 μg/dose/animal. DMSO was administered at a final concentration of 4% v/v, equivalent to the amount present in ISO-66 injections. Tumor growth rate was recorded every 2-3 days by measuring the major and minor axes of the tumors formed with a digital caliper. Measurements were transformed into tumor volume using the formula: tumor volume (cm$^3$)=major axis×minor axis×0.5. On days 34 (for C57BL/6) and 40 (for Balb/C), when mean tumor volumes of the control groups exceeded 1.5-2 cm$^3$, animals were euthanized and spleens were aseptically excised from 3 mice/group. Splenocytes were isolated from individually homogenized spleens and immediately tested for their cytotoxicity versus B16-F1, CT-26.WT, YAC-1 and WEHI-164 targets in standard 51Cr-release assays.

Cytotoxicity assay: Target cells (T) were $^{51}$Cr-labelled according to Skopeliti et al. (24) and co-cultured with the effectors (E) at the indicated E:T ratios. After 18 h at 37° C., 5% $CO_2$, 100 µL of each well's supernatant were removed and isotope was measured in a γ-counter (1275 Minigamma, LKB Wallac, Turku, Finland). Targets were incubated with 3 N HCl and in complete medium to determine maximal and spontaneous isotope release, respectively. All cultures were set in triplicates. Percentage of specific cytotoxicity was calculated according to the formula: (cpm experimental−cpm spontaneous)/(cpm maximal−cpm spontaneous)×100.

Statistical analysis: Data were analyzed by the Student's t-test and statistical significance was presumed at significance level of 5% ($p<0.05$). Tumor size among groups was compared with Wilcoxon's signed rank test.

Results

ISO-66 as an inhibitor of MIF: ISO-66, a novel analog of ISO-1, is a potent inhibitor of MIF tautomerase activity (FIG. 1). It was previously established that the ester functional group in ISO-1 plays an important role in binding to MIF, as evident by SAR studies and MIF: ISO-1 co-crystal structure (11). However, the inventors hypothesized it is possible the methyl ester may hydrolyze. This could limit the application of ISO-1. It was further hypothesized that the methyl ester could be replaced by a ketone group, but not predictable if the resultant compound would actually be active.

ISO-66 was synthesized in three steps and characterized by NMR and mass spectrometry. ISO-66 was found to inhibit MIF tautomerase activity with an $IC_{50}$ of 1.5+0.4 µM compared to 18.2+2.8 µM for ISO-1. It is superior to ISO-1 in both its potency and stability profile. To improve the solubility of ISO-66, the 3-keto carboxylate was also synthesized (referred to as KF III 53Y/prodrug of ISO-66); however it was found by mass spectrometry that KF III 53Y spontaneously decarboxylates to form ISO-66. This finding was also supported by structural studies, in which MIF was co-crystallized with KF III 53Y.

Figure 2A:
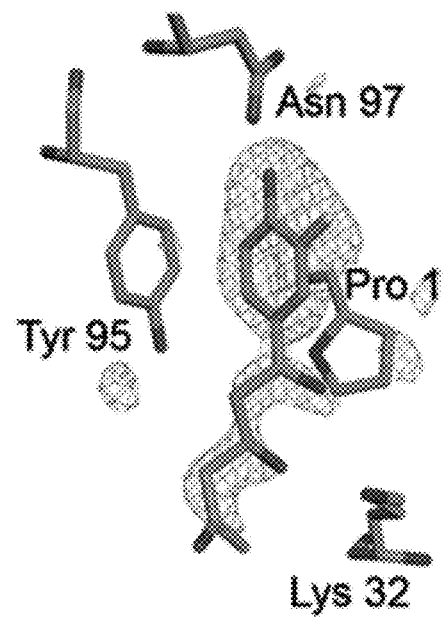
FIG. 2A-2C. Crystallographic structure of modified ISO-66 bound to MIF. Panels 2A and 2B show the Fo-Fc electron density, calculated with the omission of all inhibitor atoms, contoured at 2.5σ. 2A. The fit of the inhibitor in the solvent-exposed active site (active site C). 2B. The fit in active site B, which has better-defined density, presumably due to crystal contacts. 2C. Schematic representation of the hydrogen bonding interactions of modified KF III 53Y/prodrug of ISO-66 with MIF. Numbers listed above are distances in Ångstroms from active site C, and the lower ones are those from active site B.
Figure 2B:
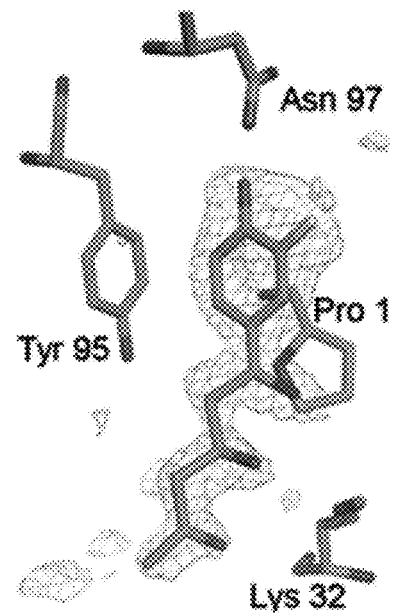
Figure 2C:
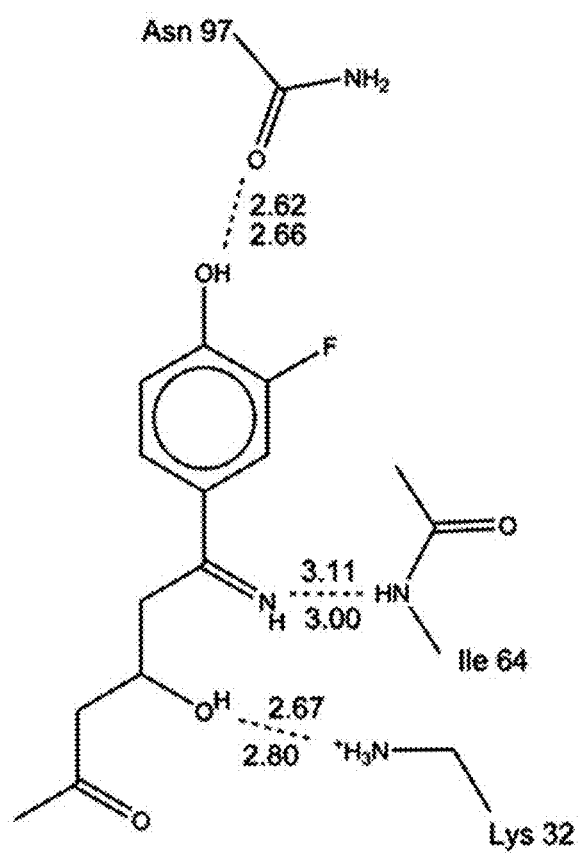

Structure of MIF-bound ISO-66: ISO-66 was found bound in the MIF tautomerase active sites, with the meta-fluoro-para-hydroxyphenyl ring buried in the innermost part of the cleft, as expected. What was unexpected, however, was that the five-membered ring of the inhibitor had been opened. The bond between the nitrogen and oxygen was cleaved, resulting in free imine and hydroxyl groups (FIG. 2). An open ring structure was seen in all three active sites. FIG. 2 shows the electron density for the inhibitor in active site C, in which no active site residues participate in crystal contacts, clearly revealing the absence of the five-membered ring. The electron density is also shown for active site B, in which the density is better defined due to the crystal contacts. The presence of the modified (ring-opened) inhibitor in the active site demonstrates that it is itself a potential inhibitor of MIF's physiological activity.

Both non-polar and polar interactions occur between the modified inhibitor and MIF. The m-fluoro-p-hydroxyphenyl ring is buried in the hydrophobic cavity of the protein. The hydroxyl group shares a hydrogen bond with Asn 97 at the base of the cavity. The fluorine atom has Van der Waals contacts with the side chain of Met 101 and the β-methylene group of His 62. Electron density for the fluorine atom is only found on one side of the ring (FIG. 2), demonstrating that the ring does not stochastically flip between two states 180° apart. Rotating the ring by 180° would cause steric conflict between the Tyr 95 and the electronegative fluorine, which would point toward the Tyr 95 aromatic π-orbital if the inhibitor's aromatic ring was in such an orientation. Lys 32 donates a strong hydrogen bond to the hydroxyl generated by the ring-opening reaction. The nitrogen that was formerly of the five-membered ring accepts a hydrogen bond from the main chain amide of Ile 64.

Figure 3A:
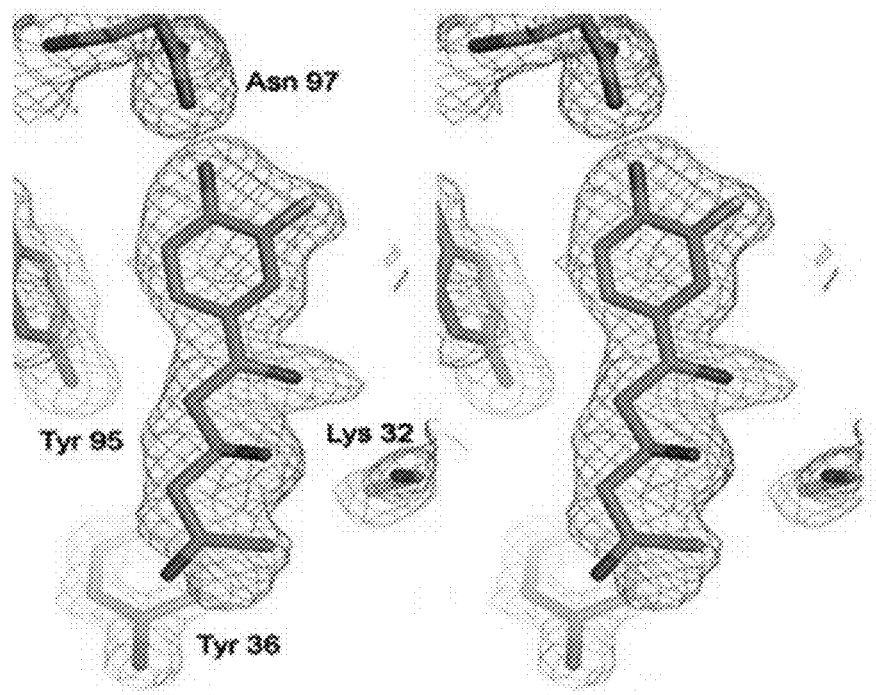
FIG. 3A-3D. Comparison of the binding of MIF with intact ISO-66 to that with the modified inhibitor. 3A. Stereo view of the modified KF III 53Y/prodrug of ISO-66, as bound in active site A. Shown is 2Fo-Fc electron density, omitting only the intact KF III 53Y/prodrug of ISO-66, contoured at 1σ. Note that, while most of the inhibitor fits the electron density, the methyl ketone group does not fit properly. 3B. The poor fit in panel A is explained by the presence of a partial occupancy inhibitor with an intact five-membered ring. The electron density map is the same shown in panel A. 3C, 3D. Comparison of the hydrogen bonding interactions between the forms with the five-membered ring open (3C) and closed (3D) in active site A. Distances are in Angstroms.
Figure 3B:
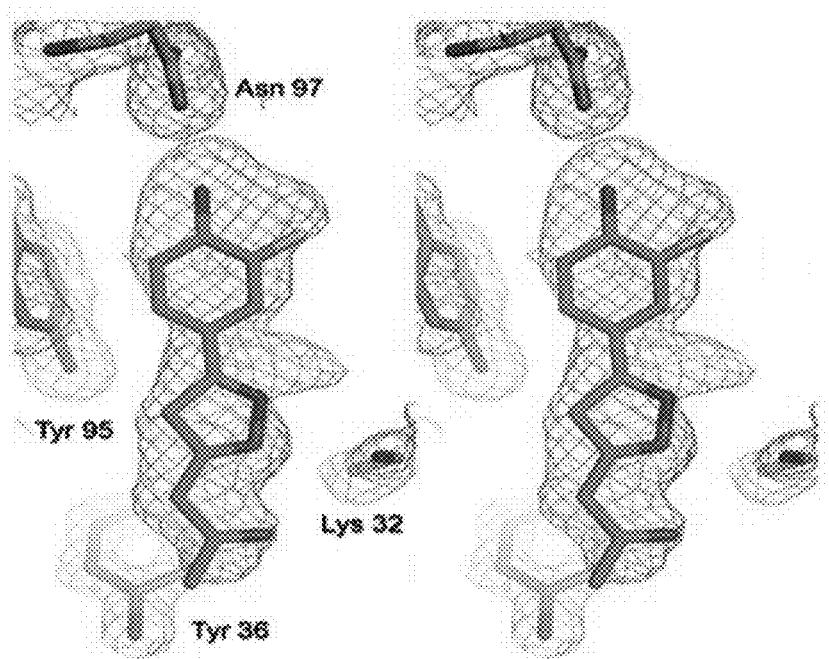
Figure 3C:
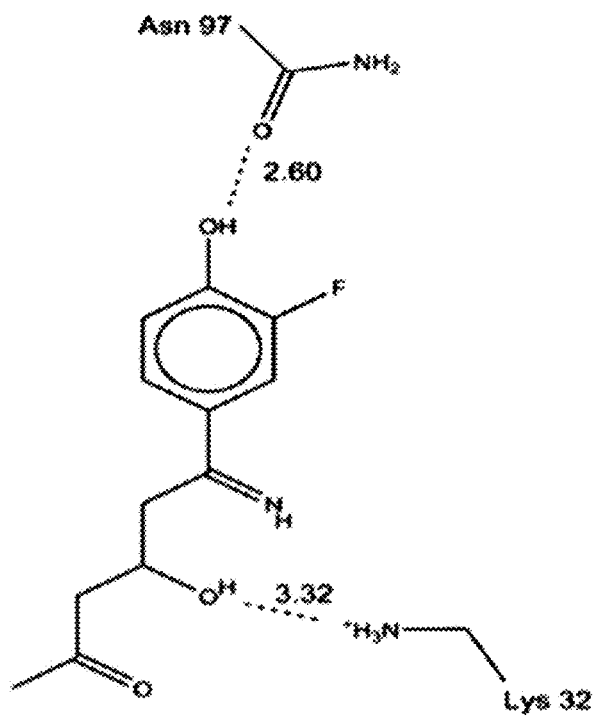
Figure 3D:
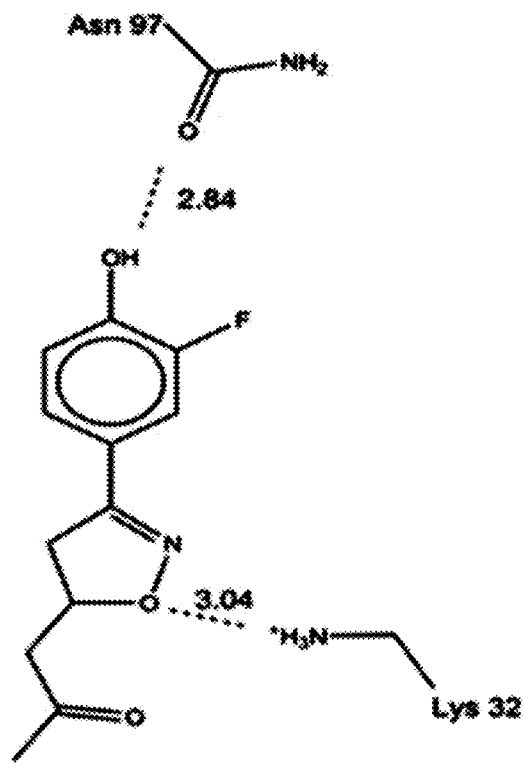

In active site A, however, there was excess electron density around the methylene and terminal methyl ketone group of the inhibitor (FIG. 3A). It is very interesting that this excess density can be explained by the intact, ring-closed form of the inhibitor, having partial occupancy (FIG. 3B). Both the ring-opened and ring-closed forms were modeled into the electron density, having occupancies of 0.88 and 0.12, respectively. The low occupancy of the intact inhibitor has no or little effect on the electron density in the phenyl portion where the B-factors for the modified inhibitor are lower than those of the intact form. However, the higher B-factors on the methyl ketone side of the modified inhibitor yields deterioration of the electron density there, where the intact form is seen instead. The intact inhibitor also accounts for the extra breadth of electron density located at the five-membered ring as shown in FIG. 3.

Both the intact and modified forms of ISO-66 interact with MIF in active site A. The interactions of the modified compound with MIF in active site A are similar to those in the other two active sites. The hydrogen bond between the nitrogen of the ring-opened inhibitor and the Ile 64 backbone amide is stretched (3.46 Å) relative to the other two active sites. The binding interactions of intact ISO-66 with MIF are as follows: Lys 32 donates a hydrogen bond to the oxygen atom of the five-membered ring and is also within hydrogen bonding distance to the ring nitrogen. The phenyl ring is positioned in the MIF hydrophobic pocket, but does not fit as deep into the cavity as the phenyl ring of the modified inhibitor. The hydroxyl group of the phenyl ring of the intact inhibitor ISO-66 shares a hydrogen bond with Asn 97. However, this is not as strong as the hydrogen bond between Asn 97 and the modified inhibitor (FIG. 3). This presents the structural view of how ISO-66 binds to its target MIF, providing a means for it to have the anti-tumor effects as described herein.

Figure 4:
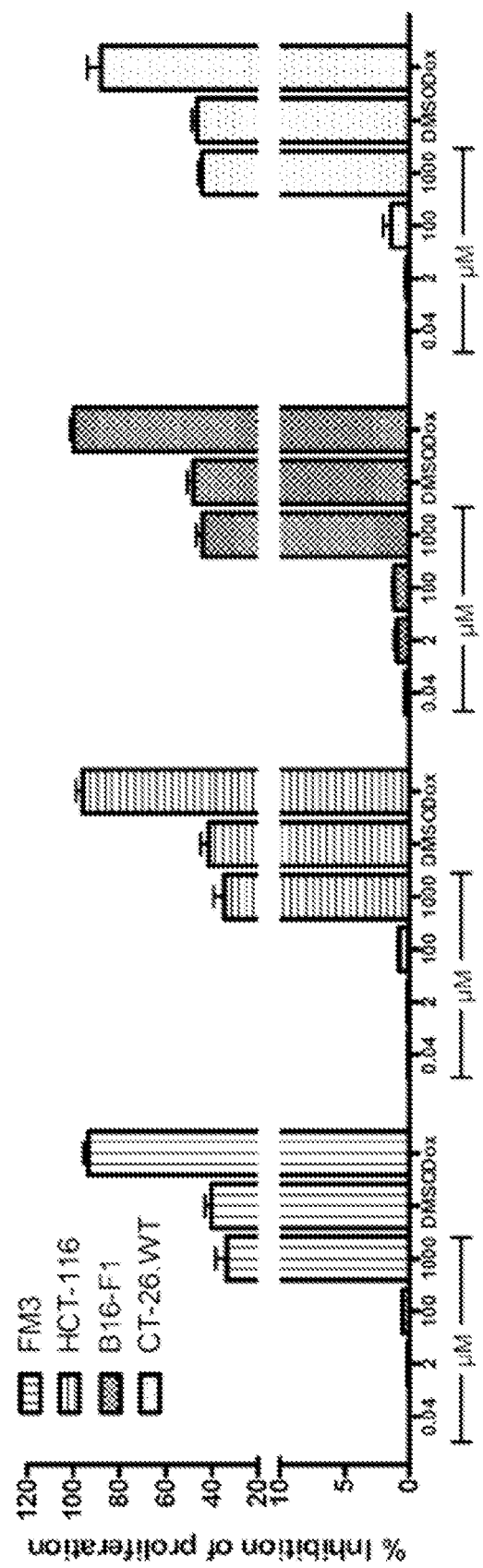
FIG. 4. ISO-66 does not inhibit cancer cell proliferation. FM3, HCT-116, B16-F1 and CT-26.WT cells were incubated with various concentrations of ISO-66 (1 mM-0.04 μM), DMSO (2% v/v) and Doxorubicin (0.5 μM) for 72 h. The percentage of DMSO corresponds to the equivalent amount used to dilute 1 mM of ISO-66.

ISO-66 does not affect cancer cell proliferation in vitro: To assess whether ISO-66 is directly cytotoxic to cancer cells, its effect in inhibiting the proliferation of the human and mouse melanoma (FM3 and B16-F1) and colon cancer cells (HCT-116 and CT-26.WT) was tested. In all experiments, the equivalent amount of DMSO (2% v/v) present in the highest ISO-66 concentration tested (1 mM), and the chemotherapeutic drug doxorubicin (0.5 µM) were used as controls. The results showed that low concentrations of ISO-66 did not affect the proliferation of cancer cells, whereas at the highest ISO-66 concentration tested, an analogous inhibition of proliferation (~50%) was also caused by the equivalent amount of DMSO (FIG. 4).

Figure 5A:
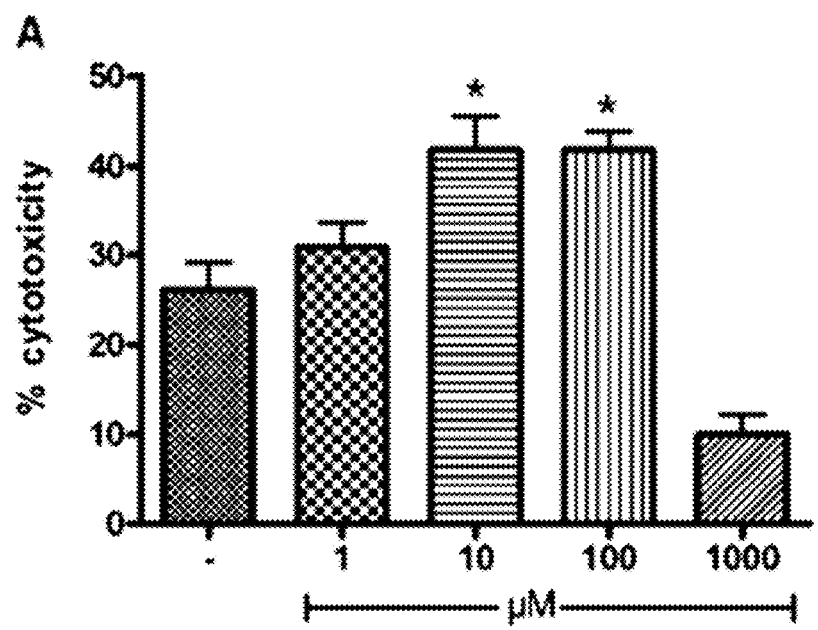
FIG. 5A-5B. ISO-66 enhances NK and LAK cell cytotoxicity. 5A. PBMCs were incubated for 3 days with ISO-66 (1 mM-1 μM), NK cells were purified and tested as effectors against K562, at an E:T ratio of 10:1. * p<0.05 compared to (−). 5B. LAK cells were incubated for 3 days with ISO-66 (10 μM) and tested as effectors against K562 (left) and Daudi (right). The E:T ratio was 50:1. Data are mean cytotoxicities±S.D. from 2-5 healthy donors. (−), cells incubated in plain medium.
Figure 5B:
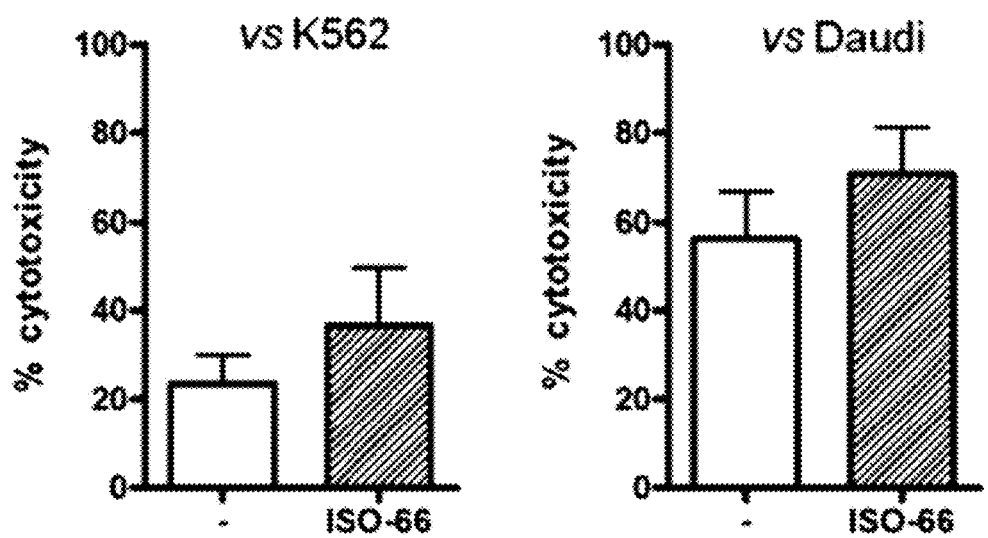

ISO-66 enhances NK and LAK cell cytotoxicity: For assessing the ability of ISO-66 to induce cytolytic PBMC responses in vitro, normal donor-derived PBMCs were incubated with 1 mM-1 µM ISO-66 for 3 days and then the CD56+ cells were isolated from the cultures. The titration experiment (FIG. 5A) showed that NK cell cytotoxicity versus K562 cell targets was equally enhanced by 16% upon incubation with 10 or 100 µM ISO-66. We further generated LAK cells from healthy donors' PBMCs and cultured them with ISO-66 for 3 days. When these were tested for their cytotoxicity, it was observed that ISO-66 increased LAK cell cytotoxicity against K562 (36.5% for ISO-66, compared to 23.5% of the control; FIG. 5B), which was further enhanced when Daudi cells were used as targets (70.7% for ISO-66, compared to 56.2% of the control; FIG. 5B). However, for both targets, this increase in LAK cell cytotoxicity did not reach statistical significance.

Figure 6A:
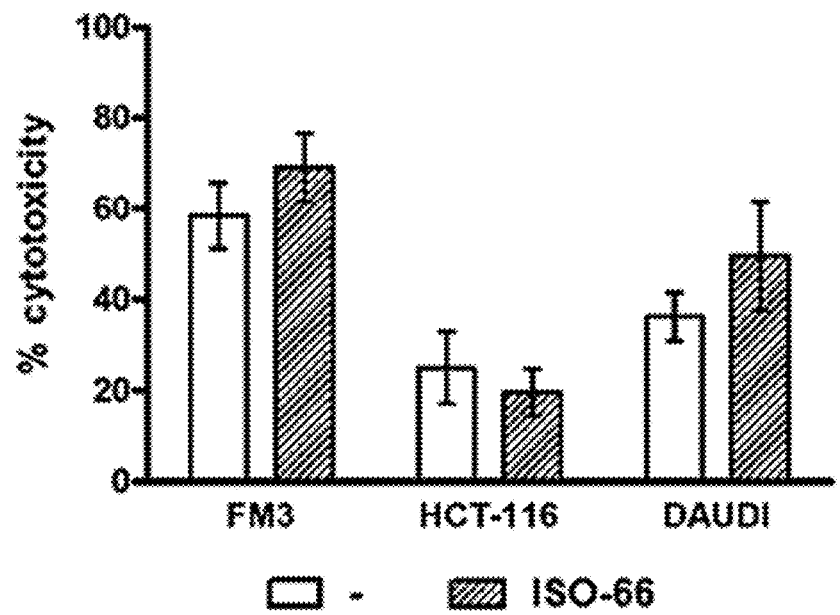
FIG. 6A-6B. ISO-66 enhances antigen-specific T cell cytotoxicity. T cells were twice stimulated with irradiated, FM3- (6A) and HCT-116- (6B) AWE-loaded autologous monocytes, in the presence of ISO-66 (10 μM). Recovered T cells were tested as effectors against FM3, HCT-116 and Daudi. The E:T ratio was 50:1. Data are mean percentage cytotoxicities±S.D. from 5 healthy donors. (−), cells incubated in plain medium.
Figure 6B:
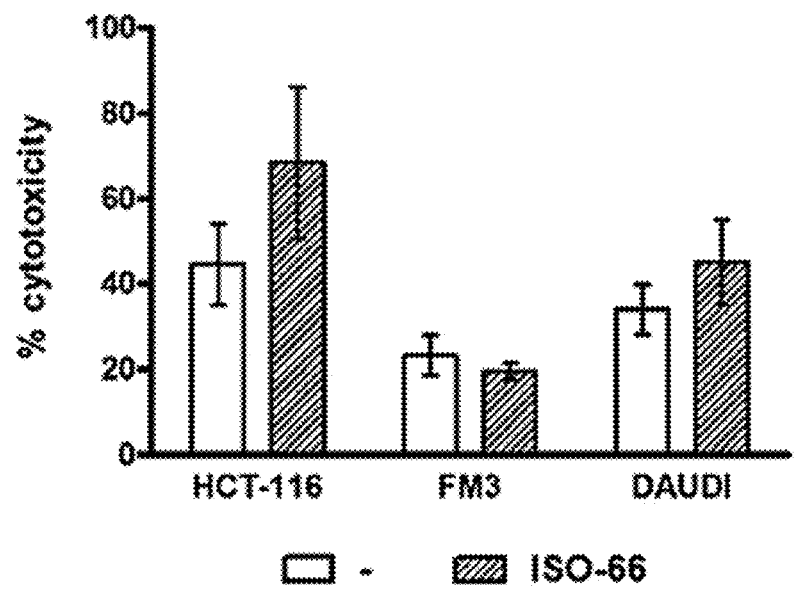

ISO-66 enhances T cell cytotoxicity: It was next sought to investigate whether ISO-66 is able to enhance T cell cytotoxicity. As specific antigen source for T cell stimulation, a pool of tumor antigenic peptides was used, detached from MHC molecules present on the surface of melanoma (FM3) and colon cancer (HCT-116) cells. In the presence of autologous irradiated monocytes as antigen-presenting cells, this extract (AWE) has been already used by us (23) and others (25) to generate in vitro tumor-reactive T cell lines. On day 5, T cells were re-stimulated with autologous AWE-loaded monocytes. To expand AWE-reactive T cells, low dose IL-2 (40 IU/ml) was used. ISO-66 was added to the cultures every other day, while cultures in plain medium served as controls. On day 11, AWE-reactive T cells cultured in the presence of ISO-66 were able to recognize and lyse more efficiently the targets used for AWE preparation (FIG. 6). Specifically, FM3-AWE-stimulated T cells killed FM3 targets (58.4%) and this cytotoxicity was enhanced in the presence of the MIF inhibitor (69.0%). The same T cells marginally lysed allogeneic HCT-116 colon cancer targets (<25%), but showed some LAK cytotoxicity (36.1% against Daudi cells), which was higher when ISO-66 was added in the cultures (49.5%; FIG. 6A). Accordingly, HCT-116-AWE-stimulated T cells killed HCT-116 targets (44.6%) and ISO-66 increased this percentage to 68.5%. HCT-116-AWE-stimulated T cells did not lyse FM3 targets (<25%) and similarly to FM3-AWE-stimulated T cells, they exhibited increased LAK activity as detected by their cytotoxicity against Daudi (45.0% for ISO-66, compared to 33.9% of the control; FIG. 6B).

ISO-66 retards melanoma and colon tumor growth in vivo: To test the anticancer activity of ISO-66 in vivo, mice were implanted with syngeneic melanoma and colon cancer cells. These two mouse models were specifically selected in order to be able to compare the results on ISO-66 with already reported data, in which MIF shRNA and ISO-1 were used to block MIF in similar in vivo melanoma and colon cancer models, respectively (3,16).

Figure 7A:
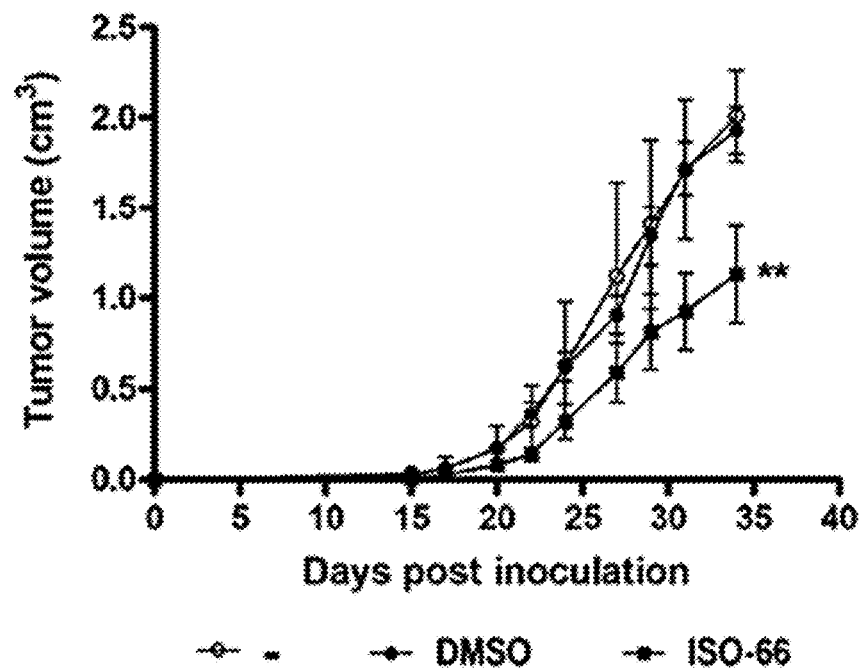
FIG. 7A-7B. ISO-66 delays melanoma and colon tumor growth. C57BL/6 (7A) and Balb/C (7B) mice were sc inoculated with syngeneic B16-F1 (melanoma) and CT-26.WT (colon cancer) cells, respectively, and ip treated with 180 μg/dose/mouse of ISO-66 for 20 consecutive days. Control mice received PBS (−) or DMSO. Tumor growth was monitored for 34 days (7A) and 40 days (7B). Pooled data from 8 mice/group are shown.  p<0.01; * p<0.001 compared to (−).

Following titration experiments (26), on day 0, C57BL6 and Balb/C mice received sc $1\times10^5$ B16-F1 or $1\times10^6$ CT-26.WT cells (melanoma and colon carcinoma syngeneic cells, respectively). By day 12-14, all mice had developed palpable tumors and were further administered ip PBS, DMSO or ISO-66 for 20 consecutive days. The dose of 180 μg ISO-66/animal/day (3.6 mg/mouse) was based on previous reports on the anticancer activity of ISO-1, where, although at different time intervals, 3.2 mg (16) and 4 mg (9) per animal were ip administered to tumor-bearing mice, without reported toxicity. In contrast to these studies, in the present protocols, ISO-66 was administered daily and for 20 consecutive days, to significantly, if not completely, inactivate MIF constantly produced both by the host and by melanoma (27) or colon cancer cells (28). Tumor growth was monitored until day 34 (for melanoma) or day 40 (for colon cancer). As shown in FIG. 7A, tumor size (expressed in $cm^3$) in melanoma-inoculated mice treated with ISO-66, showed a significantly slower increase as compared to controls (i.e., mice receiving PBS or DMSO). On the 34th day post-tumor cell inoculation, control mice were euthanized for ethical reasons (tumor size $\geq 2$ $cm^3$), whereas the average tumor volume recorded for animals treated with ISO-66 was 1.2 $cm^3$. This tumor reduction of approximately 45% was statistically significant (p<0.01, compared to controls).

Figure 7B:
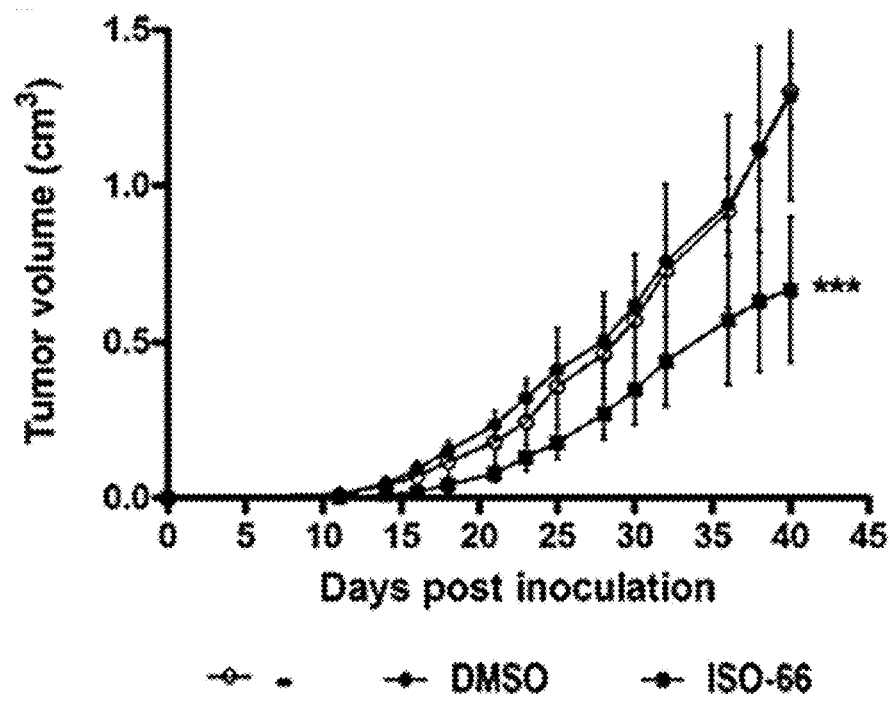

For the colon cancer model (FIG. 7B), by day 40 post-inoculation, both control groups (i.e., mice receiving PBS or DMSO) exhibited a similar rapid tumor development (1.5 $cm^3$). The therapeutic administration of the MIF inhibitor reduced tumor growth rates in all animals of the ISO-66-treated group. Specifically, the average tumor volume recorded for ISO-66 was 0.55 $cm^3$, and this ca. 60% tumor volume reduction was statistically significant compared to controls (p<0.001).

Figure 8A:
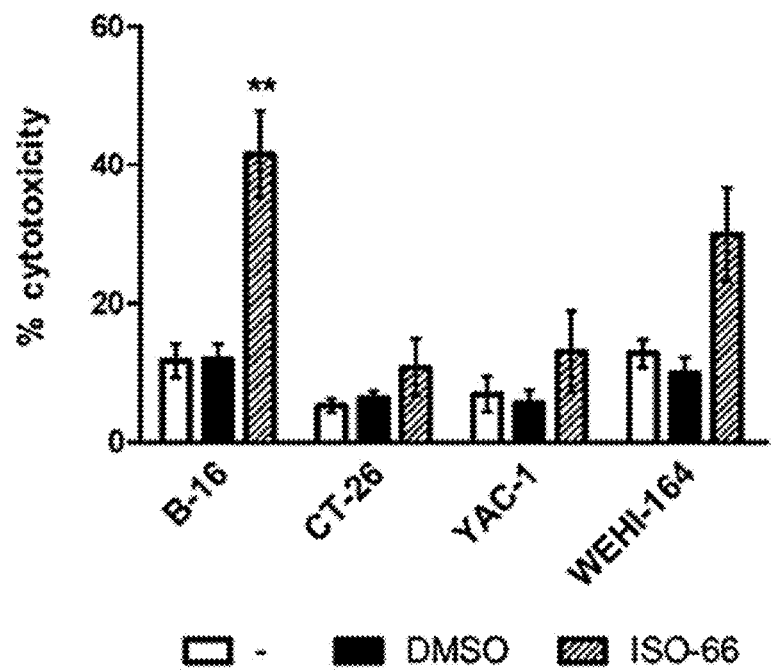
FIG. 8A-8B. ISO-66 induces tumor-reactive immune responses in vivo. Mouse splenocytes were isolated on day 34 for the melanoma (8A) and on day 40 for the colon cancer (8B) models and used as effectors versus CT-26.WT, B16-F1, YAC-1 (NK-sensitive) and WEHI-164 (LAK-sensitive) target cells, at an E:T ratio of 100:1. Data show mean specific cytotoxicity±S.D. from spleen cells of 3 mice per group (see legend of FIG. 7), tested individually. ** p<0.01 compared to (−).

The in vivo anti-tumor responses induced upon treatment with ISO-66 are mediated by T cells: To verify whether the in vivo reduction of tumor growth was associated with increased anti-tumor immune responses induced by ISO-66, three mice from each group that developed the smaller tumors were sacrificed on day 34 for melanoma and on day 40 for the colon cancer model. Without additional ex vivo stimulation, their splenocytes were used as effectors in 51Cr-release assays against the murine NK-sensitive targets YAC-1, the LAK-sensitive WEHI-164, and the syngeneic cells B16-F1 and CT-26.WT. Splenocytes from ISO-66-treated melanoma-inoculated mice were more efficient in killing B16-F1 targets than PBS- or DMSO-treated mice (41.5% versus 11.7% and 11.9%, respectively; p<0.01 compared to PBS; FIG. 8A). The same splenocytes did not lyse the non-syngeneic CT-26.WT colon targets (10.8%), or YAC-1 (13.0%), but showed some cytotoxicity against WEHI-164 (29.8% compared to 12.8% of the control; p<0.05). These results indicate that the MIF inhibitor ISO-66 increased the cytotoxicity of LAK cells and, most importantly, induced the in vivo expansion of melanoma-reactive T cells.

Figure 8B:
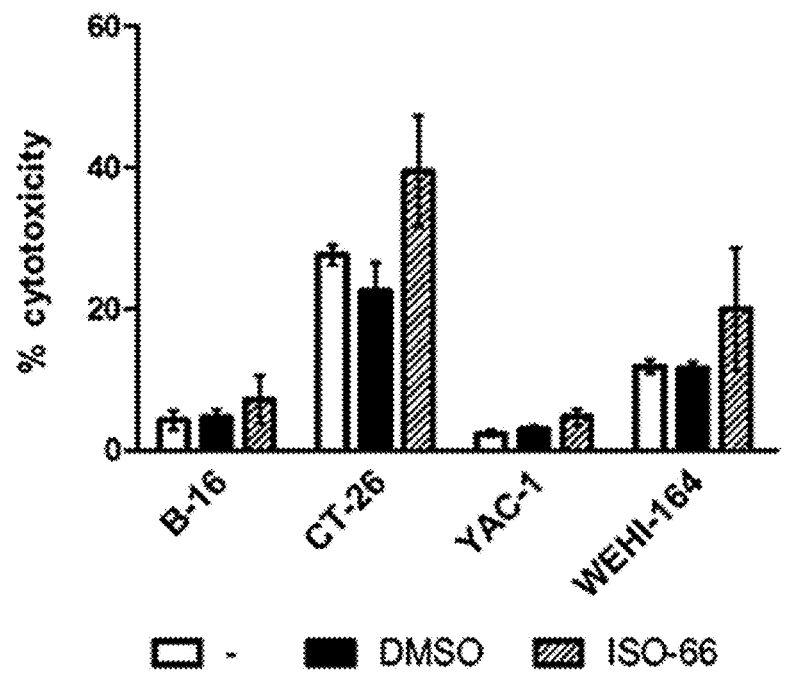

Accordingly, spleen cells from mice bearing colon cancer cells when treated with ISO-66, lysed the syngeneic CT-26.WT targets (39.4% compared to 27.6% of the PBS group; FIG. 8B), as well as the LAK-sensitive WEHI-164 (20% compared to 11.9% of the PBS group). Marginal cytotoxicity against the melanoma B16-F1 and YAC-1 was recorded. Thus, from the results obtained from both cancer models, it was observed that ISO-66 enhances tumor-reactive (T cell-mediated) and non-specific (LAK cell-mediated) immune responses leading to decreased cancer cell growth.

DISCUSSION

MIF is a pleiotropic cytokine broadly studied in sepsis and many infectious and auto-immune diseases (1). Recently, a causative role in cancer progression has been attributed to MIF, as it has been reported to inactivate p53 (29), enhance angiogenesis (30), promote metastasis (31) and impair both innate and adaptive immune responses (5,32-34). Therefore, inactivating MIF provides an alternative therapeutic option in anticancer treatment (11). Small-molecule inhibitors of host cell-derived and cancer cell-derived MIF have been used to block its activity (35). The most prominent MIF inhibitor, ISO-1, is known to inhibit the proliferation/invasiveness of cancer cell lines in vitro (9,10,13-16,36) and tumor growth and vascularization in vivo (9,16).

In this study, a more potent and more stable inhibitor of MIF than ISO-1 is presented, namely, ISO-66. In the initial in vitro studies, it was observed that ISO-66 did not affect human and mouse cancer cell proliferation, even at concentrations as high as 1 mM. ISO-66 induced the cytotoxic potential of distinct effector cell populations with antitumor activity, namely NK and LAK cells and cytotoxic T cells (CTLs) (37). Specifically, NK cells purified from human PBMCs cultured with ISO-66 showed increased killing of tumor targets (K562) and LAK cells generated with high concentrations of IL-2, when stimulated with ISO-66 efficiently lysed both K562 and Daudi targets. Most importantly, in the presence of ISO-66, tumor antigen-reactive CTLs generated in vitro, recognized and effectively killed the relative tumor-antigen expressing targets. The results are in agreement with previous reports showing that MIF hampers anticancer immunity by inhibiting tumor-specific CTL and NK cell activity (33,34). The mechanisms responsible for this CTL deficiency, probably include MIF-induced downregulation of receptors involved in tumor cell recognition (34) and/or excess T cell activation, leading to cell death (33). MIF is also known to impair the ability of NK cells to release cytolytic perforin granules (32). Additionally, it has been suggested that MIF's effect is optimally exerted on activated cells, whereas normal functions of resting cells evolve independently of MIF (9). The results are in agreement with this scenario, as NK, IL-2-activated LAK cells and antigen-stimulated CTLs, increased their cytotoxicity in the presence of ISO-66. Although ISO-1 has been reported to inhibit proinflammatory cytokine and IFN-γ secretion by human PBMCs or subpopulations thereof (38,39), the enhanced functional responses of NK, LAK and CTLs as observed in the in vitro system, do not support such an ISO-66-induced suppressive effect. More likely, ISO-66 acts by blocking the activity of MIF produced by host macrophages, possibly also T cells, allowing effectors to exert their lytic functionalities.

Translating the in vitro observations in vivo, the therapeutic anticancer activity of ISO-66 was tested in C57BL/6 and Balb/C mice inoculated with syngeneic melanoma B16-F1 and colon CT-26.WT tumor cells, respectively. In line with similar doses of ISO-1 given by others (9,16), it was observed that injecting a total of 3.6 mg of ISO-66 per mouse was well-tolerated and did not cause any adverse effects. Further, it led to a statistically significant retardation of tumor growth in both models (45% for melanoma and ca. 60% for colon carcinoma, compared to controls). Although the therapeutic protocol of the in vivo ISO-66 administration used in the study differs from other regimens used to date in terms of intervals between injections, the results are comparable with previously reported data on the anti-tumor activity both of ISO-1 and anti-MIF Abs. Specifically, He et al. (16) recorded a 25% inhibition of CT-26 colon tumors upon treatment with either ISO-1 or anti-MIF Abs administered twice per week, whereas Ogawa et al. (40) reported a much higher inhibition (55%) of the same tumor upon a more frequent (every other day) treatment with anti-MIF Abs. These data support our rationale of maximizing MIF inactivation by injecting mice with ISO-66 daily for 20 consecutive days. Of greater importance are the recent elegant studies of Girard et al. (3) and Choi et al. (4) in which MIF–/– mice inoculated with B16-F10 melanoma and CT26 colon cancer cells, respectively, exhibited a 47% and 75% tumor reduction compared to wild-type animals. Melanoma growth in wild-type mice given daily ISO-66 (FIG. 7A in this study) resembles that observed in MIF–/– mice (FIG. 3A in (3)). Similarly, colon tumor growth (FIG. 7B), greatly coincides the growth recorded in MIF–/– mice (FIG. 1A in (4)). Therefore, repetitive, daily dosing of ISO-66 effectively reduces the cancer-promoting effects of MIF.

This was further confirmed upon analyzing the ex vivo cytotoxicity of spleen cells from mice administered ISO-66 against the inoculated tumors. Splenocytes from 3 animals per group with minimal tumor load were used, as these most likely had developed the highest percentages of cytotoxic effectors. The results revealed that splenocytes from mice therapeutically administered ISO-66 exhibited increased specific lysis only of the syngeneic cancer cells, both for melanoma and colon cancer. Although a non-negligible percentage of non-specific cytotoxic responses enhanced by ISO-66 was also observed, these accounted for less than 50% of the syngeneic tumor cell killing. The results for the first time suggest that successful MIF inactivation in vivo by ISO-66 leads to restoration of the impaired tumor-reactive lymphocyte responses in cancer-bearing mice.

There are several advantages to using small molecules, such as ISO-1 or ISO-66, to block MIF activity instead of neutralizing Abs against MIF or its receptor (9,12,16,41). Small-molecule inhibitors can be developed and synthesized via a less complex and expensive process, are non-immunogenic upon repetitive administration, are more mobile in reaching their target and do not usually require intravenous injection after formulation optimization (12, 42, current report). Moreover, although administered at low concentrations, they can still effectively and specifically target MIF irrespective of its origin, i.e., whether deriving from host and/or cancer cells. Indeed, in this study 9 mg/kg of ISO-66 were shown to be non-toxic even after frequent administration and sufficient to enhance in vivo tumor-reactive immune responses leading to the reduction of tumor-cell expansion. In support of our last assumption, Yaddanapudi et al. (5) most recently reported that the suicide inhibitor of MIF, 4-IPP, significantly slowed the rate of B16 tumor growth, but to intracellularly block MIF secretion by TAMs, 4-IPP was given at doses 10-fold higher (80 mg/kg) than ISO-66 in our models, raising specificity (35) and toxicity issues, if such high concentrations were to be adapted for clinical use.

REFERENCES

1. Al-Abed Y, VanPatten S: MIF as a disease target: ISO-1 as a proof-of-concept therapeutic. Future Med Chem 3:45-63, 2011.
2. Bach J P, Deuster O, Balzer-Geldsetzer M, Meyer B, Dodel R, Bacher M: The role of macrophage inhibitory factor in tumorigenesis and central nervous system tumors. Cancer 115:2031-40, 2009.
3. Girard E, Strathdee C, Trueblood E, Queva C: Macrophage migration inhibitory factor produced by the tumour stroma but not by tumour cells regulates angiogenesis in the B16 F10 melanoma model. Br J Cancer 107:1498-505, 2012.
4. Choi S, Kim H R, Leng L, Kang I, Jorgensen W L, Cho C S, Bucala R, Kim W U: Role of macrophage migration inhibitory factor in the regulatory T cell response of tumor-bearing mice. J Immunol 189:3905-13, 2012.
5. Yaddanapudi K, Putty K, Rendon B E, Lamont G J, Faughn J D, Satoskar A, Lasnik A, Eaton J W, Mitchell R A: Control of tumor-associated macrophage alternative activation by macrophage migration inhibitory factor. J Immunol 190:2984-93, 2013.
6. Krockenberger M, Kranke P, Hausler S, Engel J B, Horn E, Nurnberger K, Wischhusen J, Dietl J, Honig A: Macrophage migration-inhibitory factor levels in serum of patients with ovarian cancer correlates with poor prognosis. Anticancer Res 32:5233-8, 2012.
7. Kindt N, Lechien J, Decaestecker C, Rodriguez A, Chantrain G, Remmelink M, Laurent G, Gabius H J, Saussez S: Expression of macrophage migration-inhibitory factor is correlated with progression in oral cavity carcinomas. Anticancer Res 32:4499-505, 2012.
8. Wang X B, Tian X Y, Li Y, Li B, Li Z: Elevated expression of macrophage migration inhibitory factor correlates with tumor recurrence and poor prognosis of patients with gliomas. J Neurooncol 106:43-51, 2012.

9. Meyer-Siegler K L, Iczkowski K A, Leng L, Bucala R, Vera P L: Inhibition of macrophage migration inhibitory factor or its receptor (CD74) attenuates growth and invasion of DU 145 prostate cancer cells. J Immunol 177: 8730-9, 2006.
10. Rendon B E, Roger T, Teneng I, Zhao M, Al-Abed Y, Calandra T, Mitchell R A: Regulation of human lung adenocarcinoma cell migration and invasion by macrophage migration inhibitory factor. J Biol Chem 282: 29910-8, 2007.
11. Lubetsky J B, Dios A, Han J, Aljabari B, Ruzsicska B, Mitchell R, Lolis E, Al-Abed Y: The tautomerase active site of macrophage migration inhibitory factor is a potential target for discovery of novel anti-inflammatory agents. J Biol Chem 277:24976-82, 2002.
12. Al-Abed Y, Dabideen D, Aljabari B, Valster A, Messmer D, Ochani M, Tanovic M, Ochani K, Bacher M, Nicoletti F, Metz C, Pavlov V A, Miller E J, Tracey K J: ISO-1 binding to the tautomerase active site of MIF inhibits its pro-inflammatory activity and increases survival in severe sepsis. J Biol Chem 280:36541-4, 2005.
13. Winner M, Meier J, Zierow S, Rendon B E, Crichlow G V, Riggs R, Bucala R, Leng L, Smith N, Lolis E, Trent J O, Mitchell R A: A novel, macrophage migration inhibitory factor suicide substrate inhibits motility and growth of lung cancer cells. Cancer Res 68:7253-7, 2008.
14. Schrader J, Deuster O, Rinn B, Schulz M, Kautz A, Dodel R, Meyer B, Al-Abed Y, Balakrishnan K, Reese J P, Bacher M: Restoration of contact inhibition in human glioblastoma cell lines after MIF knockdown. BMC Cancer 9:464, 2009.
15. Piette C, Deprez M, Roger T, Noel A, Foidart J M, Munaut C: The dexamethasone-induced inhibition of proliferation, migration, and invasion in glioma cell lines is antagonized by macrophage migration inhibitory factor (MIF) and can be enhanced by specific MIF inhibitors. J Biol Chem 284:32483-92, 2009.
16. He X X, Chen K, Yang J, Li X Y, Gan H Y, Liu C Y, Coleman T R, Al-Abed Y: Macrophage migration inhibitory factor promotes colorectal cancer. Mol Med 15:1-10, 2009.
17. Barnick J W F K, Van Der Baan J L, Bickelhaupt F. Convenient direct method for the preparation of ketoacids: Synthesis 79:787-8, 1979.
18. Rathkea M W, Nowaka M A: Synthesis of beta-keto acids and methyl ketones using bis(trimethylsilyl) malonate and triethylamine in the presence of lithium or magnesium Halides. Synthesis Communications 15:1039-49, 1985.
19. Sun H W, Swope M, Cinquina C, Bedarkar S, Bernhagen J, Bucala R, Lolis E: The subunit structure of human macrophage migration inhibitory factor: evidence for a trimer. Protein Eng 9:631-5, 1996.
20. Crichlow G V, Cheng K F, Dabideen D, Ochani M, Aljabari B, Pavlov V A, Miller E J, Lolis E, Al-Abed Y: Alternative chemical modifications reverse the binding orientation of a pharmacophore scaffold in the active site of macrophage migration inhibitory factor. J Biol Chem 282:23089-95, 2007.
21. Brunger A T, Adams P D, Clore G M, DeLano W L, Gros P, Grosse-Kunstleve R W, Jiang J S, Kuszewski J, Nilges M, Pannu N S, Read R J, Rice L M, Simonson T, Warren G L: Crystallography & NMR system: A new software suite for macromolecular structure determination. Acta Crystallogr D Biol Crystallogr 54:905-21, 1998.
22. Argyropoulou A, Samara P, Tsitsilonis O, Skaltsa H: Polar constituents of *Marrubium thessalum* Boiss. & Heldr. (Lamiaceae) and their cytotoxic/cytostatic activity. Phytother Res 26:1800-6, 2012.
23. Baxevanis C N, Voutsas I F, Tsitsilonis O E, Gritzapis A D, Sotiriadou R, Papamichail M: Tumor-specific CD4+ T lymphocytes from cancer patients are required for optimal induction of cytotoxic T cells against the autologous tumor. J Immunol 164:3902-12, 2000.
24. Skopeliti M, Voutsas I F, Klimentzou P, Tsiatas M L, Beck A, Bamias A, Moraki M, Livaniou E, Neagu M, Voelter W, Tsitsilonis O E: The immunologically active site of prothymosin alpha is located at the carboxy-terminus of the polypeptide. Evaluation of its in vitro effects in cancer patients. Cancer Immunol Immunother 55:1247-57, 2006.
25. Nair S K, Boczkowski D, Snyder D, Gilboa E: Antigen-presenting cells pulsed with unfractionated tumor-derived peptides are potent tumor vaccines. Eur J Immunol 27:589-97, 1997.
26. Ioannou K, Kavrochorianou N, Bega C, Thyphronitis G, Haralambous S, Tsitsilonis O: The C-Terminal decapeptide of prothymosin a induces a TH1-Type immune response in vitro and retards tumor growth in vivo, in, 8th Joint Conference of the International Cytokine Society and the International Society for Interferon and Cytokine Research ELSEVIER, Chicago USA, pp. 17-20, 2010.
27. Shimizu T, Abe R, Nakamura H, Ohkawara A, Suzuki M, Nishihira J: High expression of macrophage migration inhibitory factor in human melanoma cells and its role in tumor cell growth and angiogenesis. Biochem Biophys Res Commun 264:751-8, 1999.
28. Dessein A F, Stechly L, Jonckheere N, Dumont P, Monte D, Leteurtre E, Truant S, Pruvot F R, Figeac M, Hebbar M, Lecellier C H, Lesuffleur T, Dessein R, Grard G, Dejonghe M J, de Launoit Y, Furuichi Y, Prevost G, Porchet N, Gespach C, Huet G: Autocrine induction of invasive and metastatic phenotypes by the MIF-CXCR4 axis in drug-resistant human colon cancer cells. Cancer Res 70:4644-54, 2010.
29. Hudson J D, Shoaibi M A, Maestro R, Carnero A, Hannon G J, Beach D H: A proinflammatory cytokine inhibits p53 tumor suppressor activity. J Exp Med 190: 1375-82, 1999.
30. Sun B, Nishihira J, Suzuki M, Fukushima N, Ishibashi T, Kondo M, Sato Y, Todo S: Induction of macrophage migration inhibitory factor by lysophosphatidic acid: relevance to tumor growth and angiogenesis. Int J Mol Med 12:633-41, 2003.
31. Sun B, Nishihira J. Yoshiki T, Kondo M, Sato Y, Sasaki F, Todo S: Macrophage migration inhibitory factor promotes tumor invasion and metastasis via the Rho-dependent pathway. Clin Cancer Res 11:1050-8, 2005.
32. Apte R S, Sinha D, Mayhew E, Wistow G J, Niederkorn J Y: Cutting edge: role of macrophage migration inhibitory factor in inhibiting N K cell activity and preserving immune privilege. J Immunol 160:5693-6, 1998.
33. Yan X, Orentas R J, Johnson B D: Tumor-derived macrophage migration inhibitory factor (MIF) inhibits T lymphocyte activation. Cytokine 33:188-98, 2006.
34. Krockenberger M, Dombrowski Y., Weidler C, Ossadnik M, Honig A, Hausler S, Voigt H, Becker J C, Leng L, Steinle A, Weller M, Bucala R, Dietl J, Wischhusen J: Macrophage migration inhibitory factor contributes to the immune escape of ovarian cancer by down-regulating NKG2D. J Immunol 180:7338-48, 2008.

35. Xu L, Li Y, Sun H, Zhen X, Qiao C, Tian S, Hou T: Current developments of macrophage migration inhibitory factor (MIF) inhibitors. Drug Discov Today 18:592-600, 2013.
36. Binsky I, Lantner F, Grabovsky V, Harpaz N, Shvidel L, Berrebi A, Goldenberg D M, Leng L, Bucala R, Alon R, Haran M, Shachar I: TAp63 regulates VLA-4 expression and chronic lymphocytic leukemia cell migration to the bone marrow in a CD74-dependent manner. J Immunol 184:4761-9, 2010.
37. Ioannou K, Samara P, Livaniou E, Derhovanessian E, Tsitsilonis O E: Prothymosin alpha: a ubiquitous polypeptide with potential use in cancer diagnosis and therapy. Cancer Immunol Immunother 61: 599-614, 2012.
38. West P W, Parker L C, Ward J R, Sabroe I: Differential and cell-type specific regulation of responses to Toll-like receptor agonists by ISO-1. Immunology 125:101-10, 2008.
39. Chuang C C, Chuang Y C, Chang W T, Chen C C, Hor L I, Huang A M, Choi P C, Wang C Y, Tseng P C, Lin C F: Macrophage migration inhibitory factor regulates interleukin-6 production by facilitating nuclear factor-kappa B activation during *Vibrio vulnificus* infection. BMC Immunol 11:50, 2010.
40. Ogawa H, Nishihira J, Sato Y, Kondo M, Takahashi N, Oshima T, Todo S: An antibody for macrophage migration inhibitory factor suppresses tumour growth and inhibits tumour-associated angiogenesis. Cytokine 12:309-14, 2000.
41. Takahashi K, Koga K, Linge H M, Zhang Y, Lin X, Metz C N, Al-Abed Y, Ojamaa K, Miller E J: Macrophage CD74 contributes to MIF-induced pulmonary inflammation. Respir Res 10:33, 2009.
42. Imai K, Takaoka A: Comparing antibody and small-molecule therapies for cancer. Nat Rev Cancer 6:714-27, 2006.
43. Engh R A, Huber R: Accurate bond and angle parameters for X-ray protein structure refinement. Acta Cryst 47:392-400, 1991.

What is claimed is:
1. A compound having the following structure:

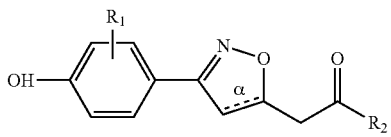

wherein bond α is either present or absent, and when bond α is absent $R_1$ is a monohalo substitution or a dihalo substitution and R2 is a C2-C10 alkenyl, a C2-C10 alkynyl, or —CH$_2$C(O)(OH), and when bond α is present $R_1$ is H, a monohalo substitution or a dihalo substitution,
$R_2$ is a C1-C10 alkyl, a C2-C10 alkenyl, a C2-C10 alkynyl, an aryl, a heterocyclic, or —CH$_2$C(O)(OH)—,
or a stereoisomer of the compound thereof or a pharmaceutically acceptable salt of the compound.

2. The compound, stereoisomer or pharmaceutically acceptable salt of claim 1, wherein the halogen of the monohalo or dihalo is F.

3. The compound, stereoisomer or pharmaceutically acceptable salt of claim 1, wherein bond α is present and $R_2$ is a C1 alkyl.

4. The compound of claim 1, having the following structure:

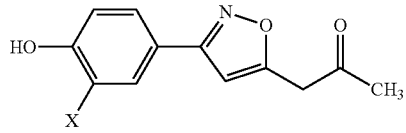

where X=H or F,
or a stereoisomer or pharmaceutically acceptable salt thereof.

5. The compound of claim 1, having the following structure:

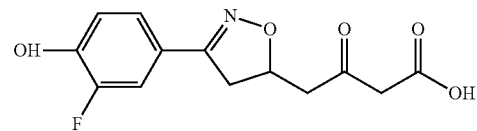 [SMILES: O=C(O)CC(=O)CC1CC(c2ccc(O)c(F)c2)=NO1]

or stereoisomer or pharmaceutically acceptable salt thereof.

6. A composition comprising the compound or stereoisomer or pharmaceutically acceptable salt thereof of claim 1, and a pharmaceutically acceptable carrier.

7. The composition of claim 6, which is a pharmaceutical composition.

8. A process for making the compound of claim 1, comprising:
   a) contacting 3-fluoro-4-hydroxybenzaldoxime with a chlorinating agent so as to produce a chloro oxime thereof; and
   b) contacting the chloro oxime with 4-penten-2-one followed by addition of suitable base thereto,
   so as to produce the compound.

9. A method of treating a tumor in a subject comprising administering to the subject the compound or stereoisomer or pharmaceutically acceptable salt of claim 1 in an amount effective to treat a tumor in a subject.

10. A method of inhibiting progression of a tumor in a subject comprising administering to the subject the compound or stereoisomer or pharmaceutically acceptable salt of claim 1 in an amount effective to inhibit progression of a tumor in a subject.

11. A method of stimulating expansion of an anti-tumor reactive effector cell in a subject comprising administering to the subject the compound or stereoisomer or pharmaceutically acceptable salt of claim 1 in an amount effective to stimulate expansion of an anti-tumor reactive effector cell.

12. The method of claim 9, wherein the tumor is a melanoma.

13. The method of claim 9, wherein the tumor is a colon cancer.

14. A method of reducing an inflammation in a subject comprising administering to the subject the compound or stereoisomer or pharmaceutically acceptable salt of claim 1 in an amount effective to reduce inflammation in a subject wherein the compound of claim 1 or stereoisomer or pharmaceutically acceptable salt thereof inhibits migration inhibitory factor (MIF).

15. The method of claim 9, wherein a compound having the structure:

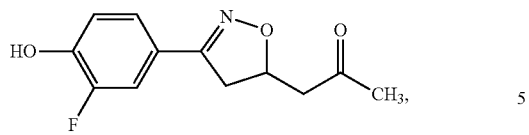

or a stereoisomer or pharmaceutically acceptable salt thereof is administered.

16. The method of claim 9, wherein the subject is human.

17. A method of manufacturing a medicament comprising admixing the compound or stereoisomer or pharmaceutically acceptable salt thereof of claim 1, and a pharmaceutically acceptable carrier.

18. A pharmaceutical composition comprising the compound or stereoisomer or pharmaceutically acceptable salt thereof of claim 1, and a pharmaceutically acceptable carrier.

19. A method of treating a tumor in a subject comprising administering to the subject the compound or stereoisomer or pharmaceutically acceptable salt of claim 1 and an anti-tumor agent, in an amount effective to treat a tumor in a subject.

20. A method of treating an autoimmune disease in a subject comprising administering to the subject the compound or stereoisomer or pharmaceutically acceptable salt of claim 1 and an anti-autoimmune agent, in an amount effective to treat an autoimmune disease in a subject wherein the compound of claim 1 or stereoisomer or pharmaceutically acceptable salt thereof inhibits migration inhibitory factor (MIF).

\* \* \* \* \*